United States Patent
Rogeau et al.

(10) Patent No.: US 7,828,823 B2
(45) Date of Patent: Nov. 9, 2010

(54) DEVICE FOR CONNECTING BONY PORTIONS

(75) Inventors: Dominique Rogeau, Barcelona (ES); Ben-Mokhtar Mourad, Geneva (ES)

(73) Assignee: Eden Spine Europe SA, Geneva (CH)

( * ) Notice: Subject to any disclaimer, the term of this patent is extended or adjusted under 35 U.S.C. 154(b) by 149 days.

(21) Appl. No.: 11/433,405

(22) Filed: May 15, 2006

(65) Prior Publication Data
US 2007/0196166 A1    Aug. 23, 2007

(30) Foreign Application Priority Data
Feb. 23, 2006   (EP)   .................... 06003652

(51) Int. Cl.
*A61B 17/70*   (2006.01)
*F16C 11/06*   (2006.01)

(52) U.S. Cl. .............. 606/256; 606/246; 606/260; 403/120

(58) Field of Classification Search ........... 403/57, 403/59, 61, 74, 120, 111; 464/112, 118, 464/120; 606/61, 246, 254–262, 264, 265
See application file for complete search history.

(56) References Cited

U.S. PATENT DOCUMENTS

| | | | | |
|---|---|---|---|---|
| 2,051,248 A | * | 8/1936 | Dunn | |
| 2,687,024 A | * | 8/1954 | George | 464/112 |
| 3,343,856 A | * | 9/1967 | Cislo | |
| 4,114,401 A | * | 9/1978 | Van Hoose | 464/120 |
| 4,133,189 A | * | 1/1979 | Rineer | |
| 4,557,335 A | * | 12/1985 | Handy | 172/44 |
| 4,576,499 A | * | 3/1986 | Smith | 403/138 |
| 4,936,701 A | * | 6/1990 | Allen et al. | 403/120 |
| 5,207,718 A | * | 5/1993 | Glover et al. | |
| 5,375,823 A | * | 12/1994 | Navas | 606/61 |
| 5,409,332 A | * | 4/1995 | Chabot et al. | 403/57 |
| 5,564,664 A | * | 10/1996 | Oschwald | 403/111 |
| 5,738,586 A | * | 4/1998 | Arriaga | |
| 6,145,416 A | * | 11/2000 | Bonniot | 403/74 |
| 6,241,730 B1 | | 6/2001 | Alby | |
| 6,244,966 B1 | * | 6/2001 | Ofenhitzer et al. | 464/112 |
| 7,261,488 B2 | * | 8/2007 | Dobson et al. | |
| 2005/0165396 A1 | | 7/2005 | Fortin et al. | |

FOREIGN PATENT DOCUMENTS

| | | | |
|---|---|---|---|
| DE | 2651168 A | * | 5/1978 |
| EP | 0 919 199 B1 | | 1/2005 |
| FR | 957616 | * | 2/1950 |
| FR | 2 697 428 | | 5/1994 |
| FR | 2 869 524 | | 11/2005 |
| JP | 10 277070 | | 10/1998 |

* cited by examiner

*Primary Examiner*—Victor MacArthur
(74) *Attorney, Agent, or Firm*—Young & Thompson

(57) ABSTRACT

A device for connecting bony portions, such as a dynamic intervertebral connection device, includes a female member (2) having a cavity (5) and intended to be connected to a first bony portion, a male member (1) articulated in the cavity (5) and intended to be connected to a second bony portion, the male member (1) having a lateral articulation surface (13) coacting with a lateral surface (6a) of the cavity (5) to guide movements of inclination of the male member (1) relative to the female member (2), and resilient elements (8) arranged to exert an action countering the inclination movements. The resilient elements (8) are disposed in a recess (10) of the male member (1) delimited laterally by a surface (12) that is opposite the articulation surface (13).

15 Claims, 3 Drawing Sheets

DEVICE FOR CONNECTING BONY PORTIONS

BACKGROUND OF THE INVENTION

1. Field of the Invention

The present invention relates to a device for connecting bony portions, in particular a device for intervertebral connection intended to correct pathological defects of the vertebral column such as lordoses, scolioses, vertebral fractures, discal hernias, etc.

2. Description of the Related Art

Such an intervertebral connection device is described in EP 0 919 199. It comprises a male rod and a female rod intended to be fixed to respective vertebra by pedicular screws. The male rod is mounted in the female rod movably in inclination and in axial translation. The male rod comprises a collar whose convex, peripheral surface constitutes a surface of articulation coacting with an internal cylindrical lateral wall of the female rod during relative movements of the male and female rods. A damping system, comprising two sets of resilient rings disposed about the male rod and on either side of the collar, damp these relative movements.

This device according to EP 0 919 199 has the drawback that the guidance of the male rod in the female rod by the mentioned articulation surface during relative movements of inclination of the rods, can take place only over a limited amplitude, for a given size of the device, because the collar is located between the two sets of resilient rings, which necessarily limits its thickness.

SUMMARY OF THE INVENTION

The present invention seeks to provide a device for connecting bony portions, whose male rod can have a greater surface of articulation, to permit a greater amplitude of guided inclination of the male rod in the female rod.

To this end, there is provided a device for connecting bony portions including a female member having a cavity and intended to be connected to a first bony portion, a male member articulated in the cavity and intended to be connected to a second bony portion, the male member including a lateral articulation surface coacting with a lateral surface of the cavity to guide inclination movements of the male member relative to the female member, the male member being movable to the female member also in axial translation, and first resilient means arranged to exert a resilient action countering the inclination movements and an axial translational movement of the male member relative to the female member, where the first resilient means is disposed in a recess of the male member, said recess being delimited at the recess's lateral outer portion by an inner surface of a wall of the male member, said articulation surface forming an outer surface of said wall opposite said inner surface.

BRIEF DESCRIPTION OF THE DRAWING FIGURES

Other characteristics and advantages of the present invention will become apparent from a reading of the following detailed description, given with reference to the accompanying drawings, in which.

DETAILED DESCRIPTION OF THE PREFERRED EMBODIMENTS

Figure 1:
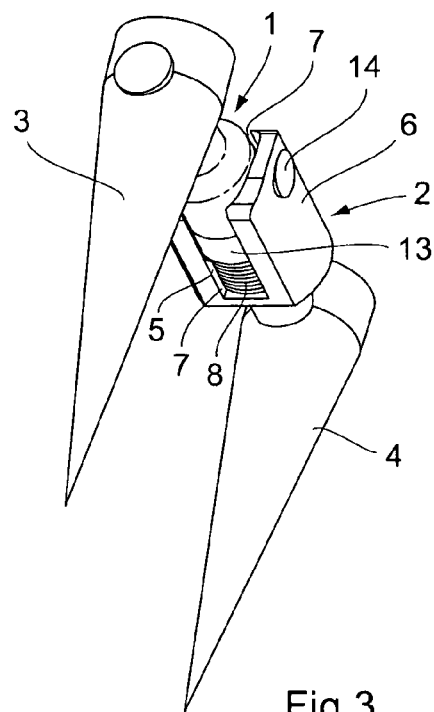
FIG. 1 is a perspective view of an intervertebral connection device according to the invention.
Figure 2:
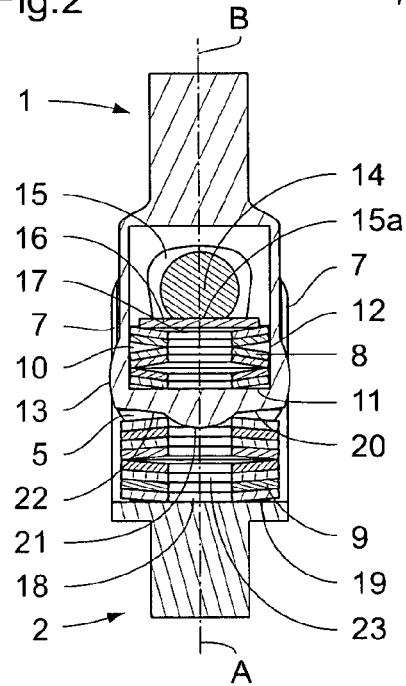
FIGS. 2 and 3 are fragmentary cross-sectional views, respectively in the sagittal plane and in the frontal plane, of the intervertebral connection device according to the invention, in a rest position.
Figure 3:
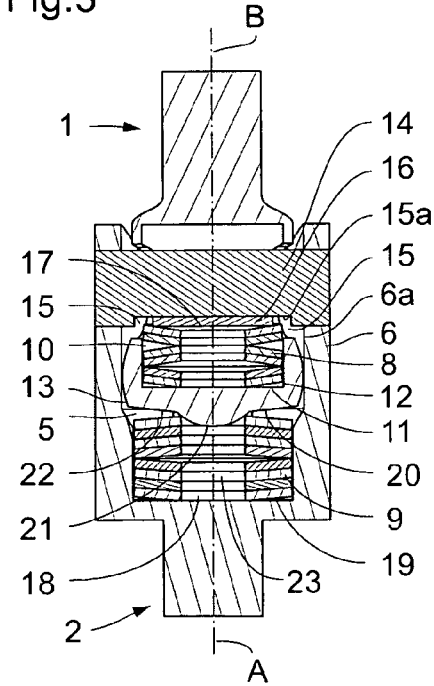

With references to FIGS. 1 to 3, a dynamic intervertebral connection device according to the invention, intended to be implanted on the posterior side of the vertebral column, comprises a male rod 1 and a female rod 2 fixed to two bone anchoring elements, such as pedicular screws 3, 4, intended to be fixed in two respective vertebrae. The female rod 2 comprises a cavity 5 in which is articulated the male rod 1. The lateral wall 6 of the female rod 2 has a cylindrical shape that is truncated in its anterior and posterior portions to reduce the dimension of the device in the anterior-posterior direction. The lateral wall 6 of the female rod 2 more precisely defines two opposite recesses 7 of U shape, leaving exposed the portion of the male rod 1 located within the cavity 5.

In the rest position, the male and female rods 1, 2 are coaxial. The male rod 1 is movable relative to the female rod 2 in axial translation, in rotation about a multitude of axes contained in a plane perpendicular to the axis A of the female rod 2 (inclination), and in rotation about its axis B (torsion). The male rod 1 can carry out movements of pure axial translation, of pure rotation, as well as combined translation-rotation movements.

The relative movements of the male and female rods 1 and 2 are damped by two springs 8, 9 disposed one in an interior recess 10 of the male rod 1 and the other in the bottom of the cavity 5. In the illustrated example, these springs 8, 9 are each in the form of a stack of truncated conical resilient rings, so called Belleville rings. The first spring 8, disposed in the interior recess 10 of the male rod 1, is constituted by three groups of two superposed Belleville rings, placed in opposition. The second spring 9, disposed in the bottom of the cavity 5, is constituted by two groups of four superposed Belleville rings, placed in opposition. The Belleville rings of the springs 8, 9 could however be arranged differently and be of different number. In a modified embodiment, the springs 8, 9 could be elastomeric rings.

The interior recess 10 of the male rod 1 in which the first spring 8 is located, is delimited by a bottom surface 11 transverse to the axis B of the male rod 1 and by a cylindrical lateral internal surface 12 of same axis as the axis B of the male rod 1. The cylindrical lateral internal surface 12 of the recess 10 is opposite a convex lateral external surface 13, in the form of a spherical segment, of the male rod 1. This convex lateral external surface 13 constitutes an articulation surface coacting with the lateral surface 6a of the cavity 5, i.e. the internal surface of the truncated cylindrical wall 6 of the female member 2, to guide the relative movements of inclination of the male and female rods 1, 2 in the manner of a rotary joint. Because this articulation surface 13 is radially facing the first spring 8, and is not below the latter, it is not or hardly limited in height (which is to say in the axial direction of the male rod 1) by this spring 8 and can thus be sufficiently large to guide the relative movements of inclination of the male and female rods 1, 2 over a large amplitude.

In a hollow portion of male rod 1, located above the recess 10 and communicating with this latter, the male rod 1 is traversed right through in the direction particular to the sagittal plane by a pin 14 fixed at its two ends to the wall 6 of the female member 2. The opposite openings 15 of the male rod 1 through which the pin 14 passes have dimensions greater than the diameter of this latter, so as to leave play between the male rod 1 and the pin 14 permitting the mentioned relative movements of translation and rotation of the rods 1, 2. The pin 14 comprises in its lower portion directed toward the bottom surface 11 of the recess 10 and the bottom surface 19 of the cavity 5, within the male rod 1, a flat 15a in which is fixed a disc-shaped flat member 16. Between this disc 16 and the bottom surface 11 of the recess 10 is freely disposed, that is to say without being fixed, the first spring 8. The flat surface 17 of the disc 16 opposite the pin 14 and the bottom surface 11 of the recess 10 serve as contact and axial bearing surfaces for the first spring 8 during operation of the device.

The second spring 9 is itself also disposed freely in the recess 18 defined by the bottom surface 19 of the cavity 5 and a lower portion of the lateral surface 6a of the cavity 5. In the rest position of the device, this spring 9 bears axially on the one hand against the bottom surface 19 of the recess 18 defined by the bottom surface 19 of the cavity 5 and on the other hand against an axial end external surface 20 of the male rod 1 opposite the bottom surface 11 of the recess 10. By this pre-stress, the spring 9 holds the rods 1, 2 in a determined relative axial position when the device is in place, vertically, in the patient. The axial end external surface 20 of the male rod 1 is constituted by a protuberant central portion 21 in the form of a spherical cap and by a peripheral portion 22 slightly in the shape of a truncated cone oriented upwardly in a radial direction from the interior toward the exterior. The protuberant central portion 21 is, in the rest position of the device, located in the central opening 23 of the spring 9 constituted by the superposition of the central openings of the Belleville rings. This protuberant central portion 21 reinforces and facilitates the lateral centering of the Belleville rings constituting the spring 9 in the recess 18.

FIGS. 4 to 11 show by way of illustration different limit positions of the device according to the invention.

Figure 4:
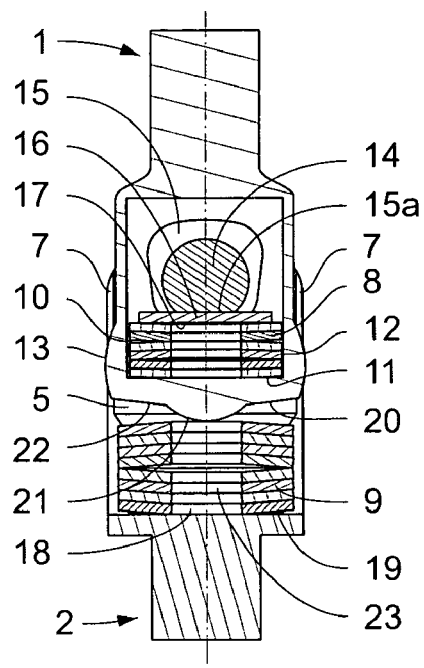
FIGS. 4 and 5 are fragmentary cross-sectional views, respectively in the sagittal plane and the frontal plane, of the intervertebral connection device according to the invention, in a limit position of axial expansion.
Figure 5:
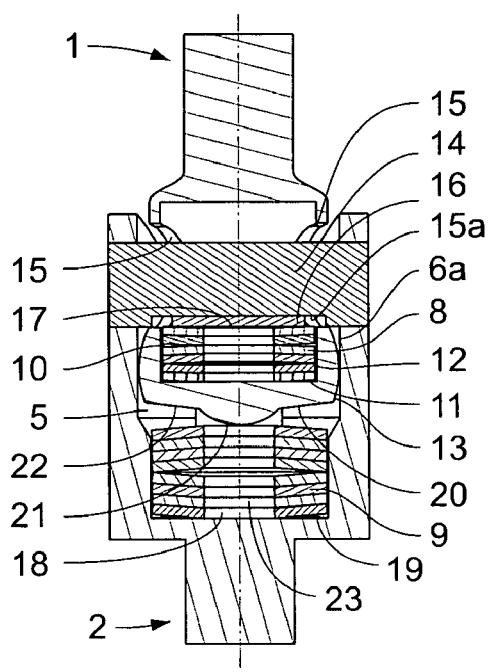

In FIGS. 4 and 5, the device has undergone a movement of axial expansion, which has axially moved apart the male and female rods 1, 2, by compressing the spring 8 between the surfaces 11, 17 and by freeing the spring 9, until the lower portion of the wall of the openings 15 of the male rod 1 abuts against the pin 14. Thus compressed, the spring 8 tends to return the rods 1, 2 to their relative rest position. In the limit position shown in FIGS. 4 and 5, the spring 9 is at rest and bears axially only on the bottom 19 of the cavity 5.

Figure 6:
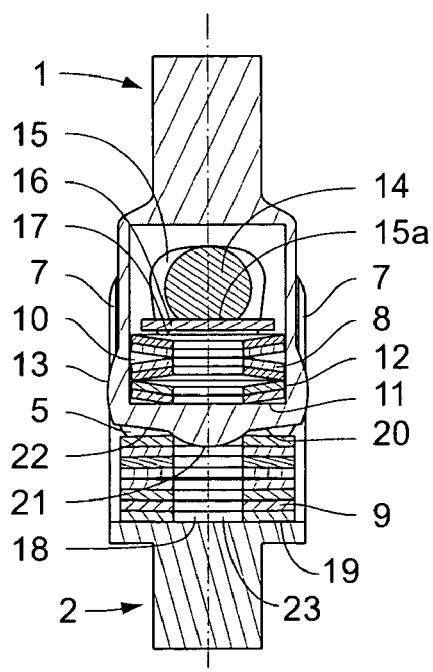
FIGS. 6 and 7 are fragmentary cross-sectional views, respectively in the sagittal plane and the frontal plane, of the intervertebral connection device according to the invention, in a limit position of axial retraction.
Figure 7:
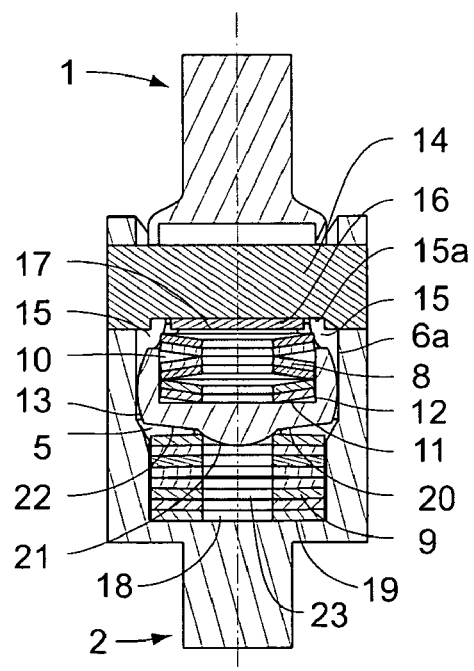

In FIGS. 6 and 7, the device has undergone a movement of axial retraction, which has axially moved closer the male and female rods 1, 2, by compressing the spring 9 between the surfaces 19, 20 and by freeing the spring 8, until the upper portion of the wall of the openings 15 of the male rod 1 abuts against the pin 14. Thus compressed, the spring 9 tends to return the rods 1, 2 into their relative rest position. In the limit position shown in FIGS. 6 and 7, the spring 8 is at rest and bears axially only on the bottom surface 11 of the recess 10.

Figure 8:
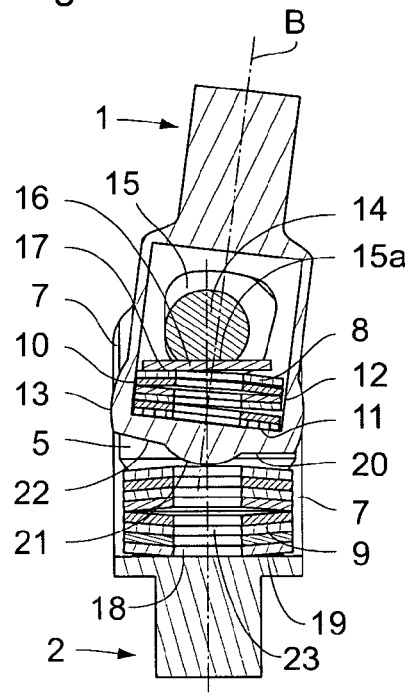
FIGS. 8 and 9 are fragmentary cross-sectional views, respectively in the sagittal plane and the frontal plane, of the intervertebral connection device according to the invention, in a limit position of inclination achieved during a flexure movement of the patient.
Figure 9:
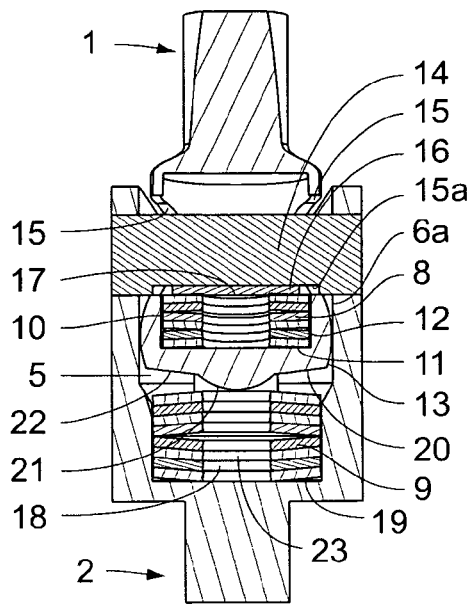

In FIGS. 8 and 9, the device is urged by a flexure movement of the patient, which movement has inclined the male rod 1 relative to the female rod 2 toward one of the openings 7 and has moved apart axially the rods 1, 2, by compressing the spring 8 asymmetrically between the surfaces 11, 17 and by freeing the spring 9, until a lower lateral portion of the openings 15 of the male rod 1 abuts against the pin 14.

Figure 10:
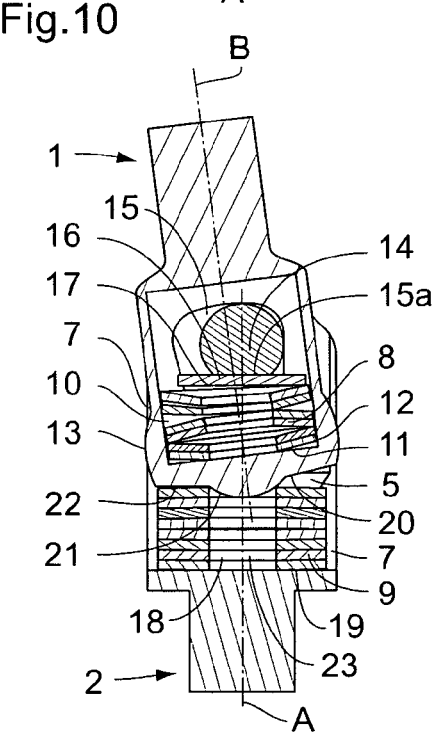
FIGS. 10 and 11 are fragmentary cross-sectional views, respectively in the sagittal plane and the frontal plane, of the intervertebral connection device according to the invention in a limit position of inclination achieved during a movement of extension of the patient.
Figure 11:
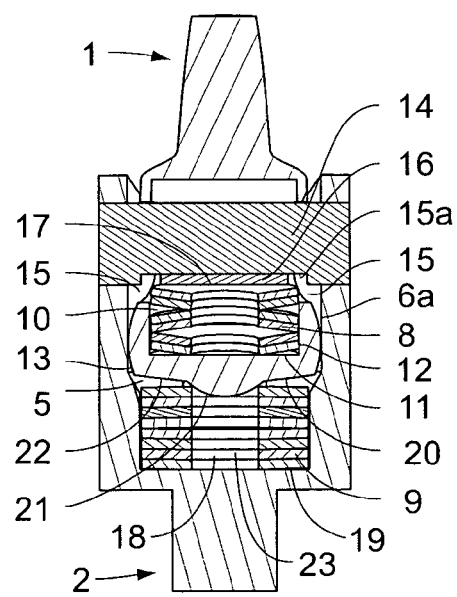

In FIGS. 10 and 11, the device is urged by an extension movement of the patient, which movement has inclined the male rod 1 relative to the female rod 2 toward the other of the openings 7 and has axially moved closer the rods 1, 2, by compressing the springs 8, 9, until an upper lateral portion of the openings 15 of the male rod 1 abuts against the pin 14.

As apparent from the examples of FIGS. 4 to 11, all the movements of the male rod 1 relative to the female rod 2 are limited in amplitude by the coaction between the pin 14 and the opening 15 of the male rod 1. In a typical embodiment of the invention, the pin 14 and the openings 15 are so dimensioned as to obtain the following movement ranges:

total angular range of inclination in flexure/extension (inclination in the sagittal plane): about 14° (±7°)

total angular range of inclination in lateral flexure (inclination in the frontal plane): about 4° (±2°)

total angular range of pivoting of the male rod 1 about its axis (torsion) when the rods 1, 2 are coaxial: about 4° (±2°)

axial range of flexure (range of axial translation between the neutral position show in FIGS. 2, 3 and the expanded limit position shown in FIGS. 4, 5 in which the rods 1, 2 are farther apart from each other): about 2 mm axial range of extension (range of axial translation between the neutral position shown in FIGS. 2, 3 and the retracted limit position shown in FIGS. 6, 7 in which the rods 1, 2 are nearer each other): about 1 mm.

It will thus be noted that the angular range of inclination in flexure/extension is sufficiently great to permit the device to adapt itself to the anatomical constraints whilst maintaining sufficient mobility and amplitude of movement. The angular range of pivoting of the male rod 1 about its axis B is itself relatively small, which avoids overloading the posterior articular system. Finally, the range of axial translation is greater, typically about twice as great, in flexure than in extension, permitting the physiological movement of the vertebral segment in question to be better respected. All these movement ranges are obtained no matter what the direction of emplacement of the device (male rod 1 up and female rod 2 down, as shown in the figures, or vice versa).

It will moreover be noted that the relative movements of the rods 1, 2 cause the springs 8, 9 to act only in compression. The springs 8, 9 are thus at each time either in a compressed state or in a rest state. Moreover, because the spring 8 is within the male rod 1, instead of about this latter, it is not urged into its central pierced portion and hence is subjected to less stress.

In a particular application of the invention, the device as described above can serve as connection between vertebrae, particularly lumbar vertebrae. The device according to the invention can however be used in other applications in which it is desired to connect bony portions together while permitting a certain mobility.

The present invention has been described above by way of example only. It will be clearly apparent to those skilled in the art that modifications can be made without departing from the scope of the invention claimed. For example, the articulation formed by the convex surface 13 of the male rod 1 and the cylindrical surface 6a of the cavity 5 could be reversed, which is to say that the surface 13 could be cylindrical and the surface 6a could comprise a convex portion. The male and female members 1, 2 could moreover be in another form than rods, for example in the form of plates, as is already known per se.

The invention claimed is:

1. An invertebral connection device, comprising:
a female member comprising a cavity and intended to be connected to a first vertebra, said cavity having an opening and a bottom surface opposite said opening;
a male member articulated in the cavity and intended to be connected to a second vertebra, the male member extending both inside and outside said cavity through said opening, the male member comprising a lateral articulation surface coacting with a lateral surface of the cavity to guide inclination movements of the male member relative to the female member, the male member being movable to the female member also in axial translation; and
first and second resilient means for damping said relative inclination and axial movements of the male and female members,
wherein the first resilient means is disposed in a recess of the male member, said recess being delimited at a recess's lateral outer portion by an inner surface of a wall of the male member, said articulation surface forming an outer surface of said wall opposite said inner surface, wherein the first resilient means is located axially between a bottom surface of said recess and a bearing member that extends transversely through the male member leaving play between the bearing member and the male member and that is fixed at the bearing member's two ends to the female member, wherein the second resilient means is disposed in the cavity and is located axially between said bottom surface of the cavity and the male member, wherein the bearing member is located axially between said opening and the bottom surface of the recess and wherein the bottom surface of the recess is axially between the bottom surface of the cavity and the bearing member.

2. The device according to claim 1, wherein the first resilient means is disposed freely in the recess.

3. The device according to claim 1, wherein the bearing member comprises a pin which passes transversely through the male member leaving play between the pin and the male member and which is fixed at the pin's two ends to the lateral surface of the cavity.

4. The device according to claim 3, wherein the bearing member comprises a flat surface transverse to the axis of the male member, the flat surface being fixed relative to the pin and serving as a contact and axial bearing surface for the first resilient means.

5. The device according to claim 1, wherein the second resilient means is disposed freely in the cavity.

6. The device according to claim 1, wherein an external bearing surface of the male member opposite the bottom surface of the recess comprises a protuberant central portion located in a central opening of the second resilient means to facilitate the lateral centering of the second resilient means in the cavity.

7. The device according to claim 1, wherein the first resilient means and the second resilient means each comprises a stack of truncated conical resilient rings.

8. The device according to claim 1, wherein the range of axial translation of the male member relative to the female member between a neutral position of the device and a first limit axial position in which the male and female members are farther apart from each other, is greater than the range of axial translation between said neutral position and a second limit axial position in which the male and female members are nearer to each other.

9. The device according to claim 1, wherein a lateral wall of the female member defining the lateral surface of the cavity has a cylindrical shape that is truncated to reduce a dimension of the device.

10. The device according to claim 1, wherein the articulation surface of the male member is convex and coacts with a cylindrical portion of the lateral surface of the cavity.

11. An osseous connection device, comprising:
a female member comprising a cavity, the female member being configured to be connected to a first vertebra, said cavity having an opening and a bottom surface opposite said opening;
a male member articulated in the cavity and configured to be connected to a second vertebra, the male member extending both inside and outside said cavity through said opening, the male member comprising a lateral articulation surface coacting with a lateral surface of the cavity to guide inclination movements of the male member relative to the female member, the male member being movable to the female member also in axial translation; and
first and second resilient means for damping said relative inclination and axial movements of the male and female members,
wherein the first resilient means is disposed in an interior recess of the male member, said recess being defined by a wall of the male member,
wherein the first resilient means is located axially between a bottom surface of said recess and a bearing member that extends transversely through the male member leaving play between the bearing member and the male member and that is fixed at the bearing member's two ends to the female member, wherein the second resilient means is located axially between said bottom surface of the cavity and the male member, wherein the bearing member is located axially between said opening and the bottom surface of the recess and wherein the bottom surface of the recess is axially between the bottom surface of the cavity and the bearing member.

12. The device according to claim 11, wherein the first resilient means is disposed freely in the recess.

13. The device according to claim 11, wherein the bearing member comprises a pin which passes transversely through the male member leaving play between the pin and the male member and which is fixed at the pin's two ends to the lateral surface of the cavity.

14. The device according to claim 13, wherein the bearing member comprises a flat surface transverse to the axis of the male member, the flat surface being fixed relative to the pin and serving as a contact and axial bearing surface for the first resilient means.

15. The device according to claim 11 wherein the second resilient means is disposed freely in the cavity.

* * * * *